(12) United States Patent
Dankwart-Eder

(10) Patent No.: US 6,493,576 B1
(45) Date of Patent: Dec. 10, 2002

(54) METHOD AND APPARATUS FOR MEASURING STIMULUS-EVOKED POTENTIALS OF THE BRAIN

(75) Inventor: Franz Dankwart-Eder, Kist (DE)

(73) Assignee: Erich Jaeger GmbH (DE)

(*) Notice: Subject to any disclaimer, the term of this patent is extended or adjusted under 35 U.S.C. 154(b) by 0 days.

(21) Appl. No.: 08/874,899

(22) Filed: Jun. 13, 1997

Related U.S. Application Data (60) Provisional application No. 60/020,135, filed on Jun. 20, 1996.

(30) Foreign Application Priority Data

Jun. 17, 1996 (DE) .......................................... 196 24 133

(51) Int. Cl.$^7$ ................................................. A61B 5/04
(52) U.S. Cl. ...................................................... 600/544
(58) Field of Search ................................... 600/544, 545

(56) References Cited

U.S. PATENT DOCUMENTS

| | | | |
|---|---|---|---|
| 4,462,411 A | * 7/1984 | Rickards | ..................... 600/544 |
| 4,557,270 A | 12/1985 | John | |
| 5,023,783 A | * 6/1991 | Cohen et al. | .................. 28/920 |
| 5,699,808 A | * 12/1997 | John | ........................... 600/483 |
| 6,067,467 A | * 5/2000 | John | ........................... 600/544 |

FOREIGN PATENT DOCUMENTS

| | | |
|---|---|---|
| DE | 3246261 | 3/1984 |
| EP | 0449574 | 2/1991 |

OTHER PUBLICATIONS

T. Takaki, "EEG Enhancement During Electrosurgery . . . " Medical & Biological Engineering & Computing Jul. 1988, pp. 397–403.

R. Bender et al, "Identification of EEG Patterns . . . " Biomedizinische Technik 10/1991, pp. 236–240.

D. Schwender et al, "Do Auditory Evoked Potentials . . . " Theoretical Surgery, 8/93, pp. 29–37.

D. Schwender et al, "Anesthetic Control of 40–Hz Brain . . . " Consciousness and Cognition, 3/94, pp. 129–147.

D. Schwender et al, "Midlatency Auditory Evoked Potentials . . . " Anaesthesia, vol. 49, 1994, pp. 99–104.

* cited by examiner

*Primary Examiner*—Kevin Shaver
*Assistant Examiner*—Navin Natnithithadha
(74) *Attorney, Agent, or Firm*—Cook, Alex, McFarron, Manzo, Cummings & Mehler, Ltd.

(57) ABSTRACT

For measurement and display of auditory evoked potentials of the brain, pickup electrodes (A, Ref), an amplifier circuit (1 . . . 5) and an evaluation facility (7) are used to display the time trend of midlatency auditory evoked potentials (MLAEP) and simultaneously therewith, during measurement of the information signals, the time trend of early brain stem auditory evoked potentials (BAEP), which is displayed at a higher time resolution as compared to the information curve. For this purpose an amplifier circuit is used the isolation stage (8) of which is arranged in a way so that the total gain of the amplifier unit (1, 3) connected between electrode assembly (A, Ref) and isolation stage (8) amounts to between approximately 1000 and 4000. A further improvement is achieved by connecting the inputs of the amplifier circuits, which are connected to one pick up electrode (A, Ref) each and to a reference potential (ground) via an input terminating resistor, to a current generator included in an impedance measuring circuit for measuring electrode impedance.

13 Claims, 7 Drawing Sheets

METHOD AND APPARATUS FOR MEASURING STIMULUS-EVOKED POTENTIALS OF THE BRAIN

This application claims the benefit of Provisional application No. 60/020,135, filed Jun. 20, 1996.

This invention pertains to a method and a test assembly for measurement and display of stimulus-evoked potentials of the brain, especially for monitoring analgesia and anesthetic depth.

During surgery it has to be assured that the patient will not wake up from general anesthesia and especially that pains during surgery or other surgical manipulations will neither be perceived during surgery nor remembered post-surgically by the patient. The fright caused by an experience like this may result in a so-called post-traumatic stress syndrome. For this reason, it is of great interest to measure and display suitable parameters which determine anesthetic depth and analgesia to enable anesthetists to control anesthesia more precisely than previously and to reduce patient strain to a minimum. In particular, undesired awakenings of the patient during anesthesia have to be realized as early as possible.

We know different methods to detect wake stages during general anesthesia. The most important (1) are the so-called PRST-score, calculated from changes of blood pressure, heart rate, sweating and tear production, and (2) the isolated forearm method, during which one of the patient's forearms is isolated against anesthesia by interrupting the blood flow by means of, for example, a hemomanometer cuff. To monitor conciousness the patient will then be examined whether he is able to adhere to simple commands during surgery. Furthermore, an EEG processing method is known, which evaluates EEG frequency and amplitude changes occurring during wake and anesthetic stages. However, the PRST score is not always a reliable method to detect intraoperative wake stages. The isolated forearm method can only be applied over a short period of time and is consequently not suited to indicate motor responses of the patient during long-lasting procedures. The processed EEG and its resulting parameters (median frequency and spectral cut-off frequency) are not optimally suited for this purpose, too.

Stimulus-evoked EEG signals, such as visually evoked potentials, somato-sensory evoked potentials and auditory evoked potentials, which will undergo dose-dependent suppression during general anesthesia, are better suited to fulfill this task. With midlatency auditory evoked potentials this dose-dependent effect becomes especially obvious. Auditory evoked potentials consist of a series of positive and negative voltages generated at different sites along the auditory pathway which can be picked up by electrodes at the skull. They reflect collection, transmission and processing of acoustic information from the cochlea via the brain stem to the cerebral cortex. Early auditory evoked potentials are generated by structures of the peripheral auditory pathway and the brain stem. They give evidence of stimulus transduction and primary stimulus transmission. It is known that early auditory evoked potentials remain almost stable during anesthesia in contrast to dose-dependent suppressed midlatency auditory evoked potentials.

In general, stimulus evoked potentials are well suited for monitoring anesthetic depth as well as for recording further neurophysiological functions. Change of the time course of the measured potentials in comparison to the unchanged potentials make it possible to draw conclusions for the neurophysiologic function to be observed. Previously, it has been difficult to apply this method practically. This was due to the fact that there were no satisfying possibilities for measuring and evaluating the potentials, especially when the measurement could not be performed under laboratory conditions but, for example, in the operating room. Under suboptimal conditions many difficulties may occur. Maybe the staff is not familiar with recording of evoked potentials or the anesthetist does not know how to interpret the recorded curves. It needs experienced experts to assess the results and to operate the equipment mentioned. Furthermore, the electrodes have to be applied simply and quickly. Other problems may occur by interference due to specific instruments in the operation room and by signals of other equipment induced into the electrodes. Besides, attending measures on the patient may give rise to movement artifacts.

Amplifier circuits, normally used for recording cerebral potentials, may be a further source of problems. They normally consist of an instrumentation amplifier, which transfers the incoming signal (typically 0.5 to 10 $\mu V$) via a high-pass filter, a mid-amplifier, a low-pass filter and a post-amplifier to an A/D converter coupled with an evaluation unit. Patient and analysis unit must be isolated from each other by, for example, an isolation amplifier, type BF or CF, to prevent inadmissible currents from passing through the electrodes if external voltages are applied.

In known circuits, this isolation unit is located either after the first amplifier stage, i.e. after a gain between 10 and less than 100, or after total gain of up to $10^6$ or after the A/D converter. This results in various disadvantages. In the first case extremely small signals pass through lines which impose a capacitive load on the driving amplifier and consequently may give rise to signal distortion. Furthermore, interference decoupling is limited, even with low driver impedance. However, if isolation is intended to be introduced after total gain, decoupling of interference will be good; indeed, the required number of components does not allow for the desired miniaturization of the circuit. Consequently, the distances to the recording sites are longer than desired for optimal recording. Besides, coupling of the output signals into the input circuit can not definitely be avoided in small sized amplifiers with high gains (from about 5000 onwards). Gains, as high as those required for measurement of evoked potentials, may cause a feedback from the amplifier output to its input, either via direct capacitive coupling or via the supply voltage. This feedback is especially disturbing if the terminating impedance of the input amplifier is high or asymmetrical. A feedback loop will change the frequency vs. time behavior of the amplifier system so that instabilities may occur which may give rise to amplifier oscillations. This is aggravated by the fact that these effects will often only give rise to minimal changes of the entire amplified signal, but will have considerable effect on the portion to be measured, which is "hidden" in the entire signal. For example, the brainstem auditory evoked potentials (BAEP) having a signal amplitude of 1 $\mu$Vss cannot be recognized in the spontaneous EEG, which has an amplitude of 20 $\mu$Vss to 50 $\mu$Vss. The BAEP can best be measured by means of averaging, provided that the spontaneous portion of the EEG averaged over time does not correlate with BAEP and that the BAEP portions occur time-synchronous after the stimulation signal. This cannot be assured, if the time behavior of the amplifier is subject to change or non-linearities due to intermodulation distortion occur. The recording signals are distorted or disappear during averaging. Another side-effect is that common mode rejection deteriorates due to positive feedback on the input. Furthermore, the system can encounter an unfavorable operation point for a short period due to common mode interference such as mains hum, monitor interference and transients. Often these instabilities are hardly visible in a single signal sweep but show their effects after averaging. The signal to noise ratio can deteriorate considerably so that the measured signals can not be analyzed any more.

The invention is intended to avoid the problems mentioned and to provide a method, and a test assembly, which allow easy, reliable and trouble-free measurement of neurophysiological signals, so that correct measurements can be performed which can be reliably assessed and which do not require experienced experts for operating the instrument being part of the test assembly.

This task is fulfilled by the features states with the patent claims.

According to a further aspect of the invention, the time trend of the evoked potentials from the brain stem (BAEP) will be displayed with a higher resolution as compared to the information signals during measurement and display of the potentials related to the function measured (MLAEP).

It is of special importance, that the reference curve or other curve (i.e. availability of reference or other curve data) are displayed during the measurement or simultaneously with the information signals. Just as the information curve, the display is automatically controlled by the computer integrated in the evaluation unit.

The invention allows for easy and reliable evaluation of the recorded signals, even under sub-optimal conditions, e.g. during surgery. This is especially useful for monitoring anesthetic depth. As the curve of the brainstem evoked potentials does not change during anesthesia and can be evaluated reliably due to a higher time resolution, it can be taken as a standard for the quality of the recorded information signals. Deterioration of the reference curve can be assumed to be due to bad recording conditions.

The evaluation of the signals will be most favorable and informative due to the fact that according to this invention the evoked stimuli will be repeated periodically or stochastically and that the actual information curve is displayed after a predefined time or number of recording periods but has been averaged over a considerably greater period of time or a considerably higher number of previous recording periods. In this context it is useful that for averaging over a predefined number of recording periods the average values of the signals recorded over a considerably lower number of recording periods will be compared automatically with each other and will be averaged themselves whereby averages that differ greatly from the majority of the other averages will be neglected. By correlating sub-groups, artifacts can be detected more easily and can be eliminated.

It may be of special advantage, if the time trend of the variation of a characteristic peak of the midlatency auditory evoked potentials (MLAEP) and/or the latency of this peak and/or the automatically calculated quotient of these two factors is displayed.

Furthermore it is useful that the time trend of a variable instrument factor is calculated by the evaluation unit and displayed simultaneously with the time trend of the recorded values. This is an additional feature which assures good quality of the measurement.

For evaluating the evoked potentials the typical amplification should be between $10^5$ and $10^6$. According to a further aspect of the invention, the total gain of the amplifier part between the electrodes and the isolating amplifier is considerably higher than 100 but less than $10^4$. The post-amplifier between the isolation amplifier and the evaluation unit takes over the remaining amplification. If, for example, the gain prior to the isolation amplifier is between 1000 and 4000, a post-amplification of more than 25, but typically between 100 and 1000, is required. This allows for the best possible compromise between the highest achievable common mode rejection (gain as high as possible before isolation stage) and a minimal coupling into the input (gain as low as possible before isolation stage). With gains of about 1000, the common mode rejection ratio can amount to 150 dB.

At the same time, the input and output circuits will be decoupled after 1000 fold gain due to the isolation stage, so that instabilities of the amplifier will no longer be expected. The output signal with the highest amplitude will then be decoupled from the supply voltage of the input circuit. At the same time, the output signal will be treated as a common mode signal by the input circuit. A further improvement can be achieved if the ground of the output circuit is connected to earth. This will considerably simplify operation of the test assembly.

The direct test assembly furthermore provides the advantage that the required amplifier circuit can be optimally miniaturized without having to cope with disadvantages such as long leads to the recording sites, signal distortion, insufficient noise decoupling and noise signals, etc.

Reliability can also be improved with further steps of development by connecting an impedance circuit for recording electrode impedance to the inputs of the amplifier circuits which, after having exceeded a limit value and/or after having reached a certain difference between e.g. the active and the reference electrode, will generate a warning signal. Wrong electrode impedances which are mainly due to the contact between electrodes and skull can cause recording errors in connection with the invention-type amplifier of the invention.

As already mentioned, the invention is not only suitable for determining anesthetic depth but also for recording any visually evoked potentials. The following description of the invention is mainly based on measurements of auditory evoked potentials for monitoring anesthetic depth.

Figure 1:
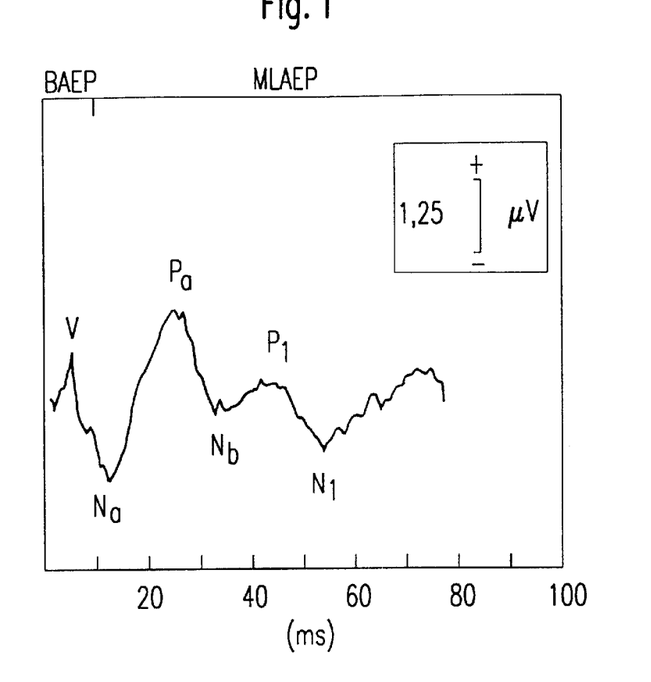
FIG. 1 illustrates the time trend of auditory evoked potentials recorded with a patient in wake condition

As is known, the time trend of auditory evoked potentials measure before and during surgery yields important information about the patient's level of anesthesia. The acoustic stimulus may be a simple click applied via headphones with a suitable typical reproduction rate of 9 to 10 Hz. This especially records evoked potentials of up to 100 ms after stimulus onset, whereby we have to differentiate between the brain stem acoustically evoked potentials (BAEP) and midlatency auditory evoked potentials (MLAEP). FIG. 1, shows the trend of the potentials recorded with the patient at wake. The first five peaks of a supraliminal stimulus of 60 dB are between 1.5 ms and 6 ms in healthy individuals, whereas the MLAEP peaks Na, Nb and N1 are between approximately 10 ms and 100 ms (N and P stand for negative and positive). As is known from literature, the MLAEP signals will be suppressed in dependency of dose during anesthesia. The amplitude of MLAEP-specific peaks decreases with increasing level of anesthesia while latencies will be expanded. In contrast to raw-EEG data it is therefore possible to realize this change of anesthetic depth already several minutes before waking-up will be indicated. This makes it possible to take early measures to prevent the patient from waking up during anesthesia. However, for correct and reliable recording and analysis of the MLAEP signals a possibility for comparison is required. The method described in this specification provides this possibility because the early BAEP signals will remain almost constant independent of the level of anesthesia.

Figure 2:
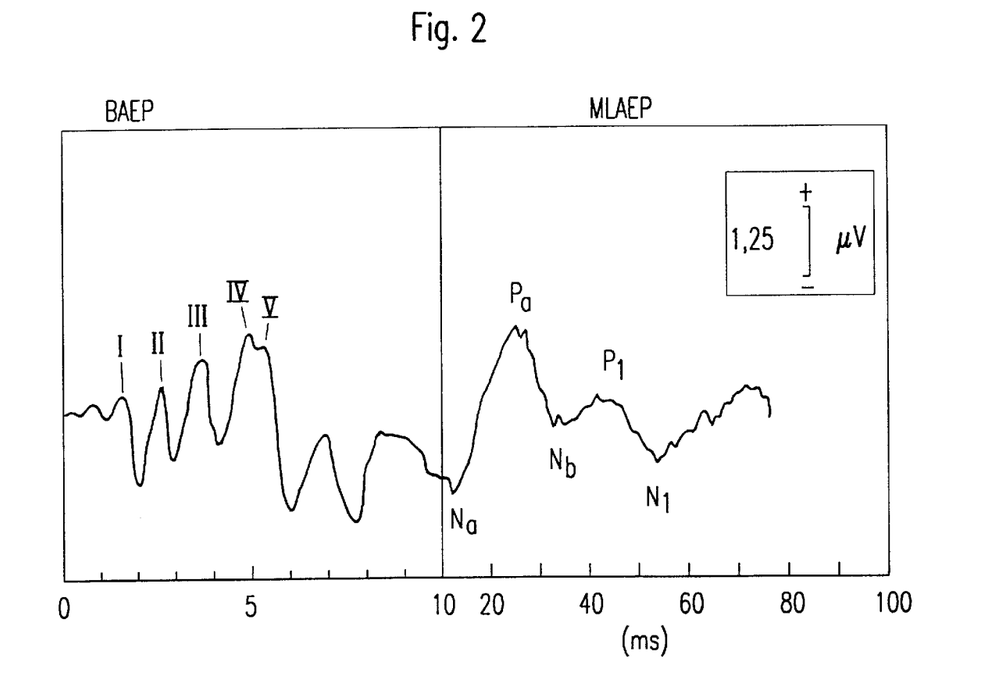
FIG. 2 illustrates curves of the recorded potential according to FIG. 1 and corresponding to the invention.

As it is quite difficult to evaluate the measurement of the BAEP signals occurring only shortly after stimulus onset (see FIG. 1), the BAEP curve is displayed with a higher time and amplitude resolution. FIG. 2 shows an example. Here the BAEP curve is "stretched" so that the width of the BAEP curve between 0 and 10 ms will be similar to the width of the MLAEP curve between 20 and 100 ms. This actually implies that it is considerably wider than the MLAEP curve when recording takes place with the same time resolution (FIG. 1).

Figure 3:
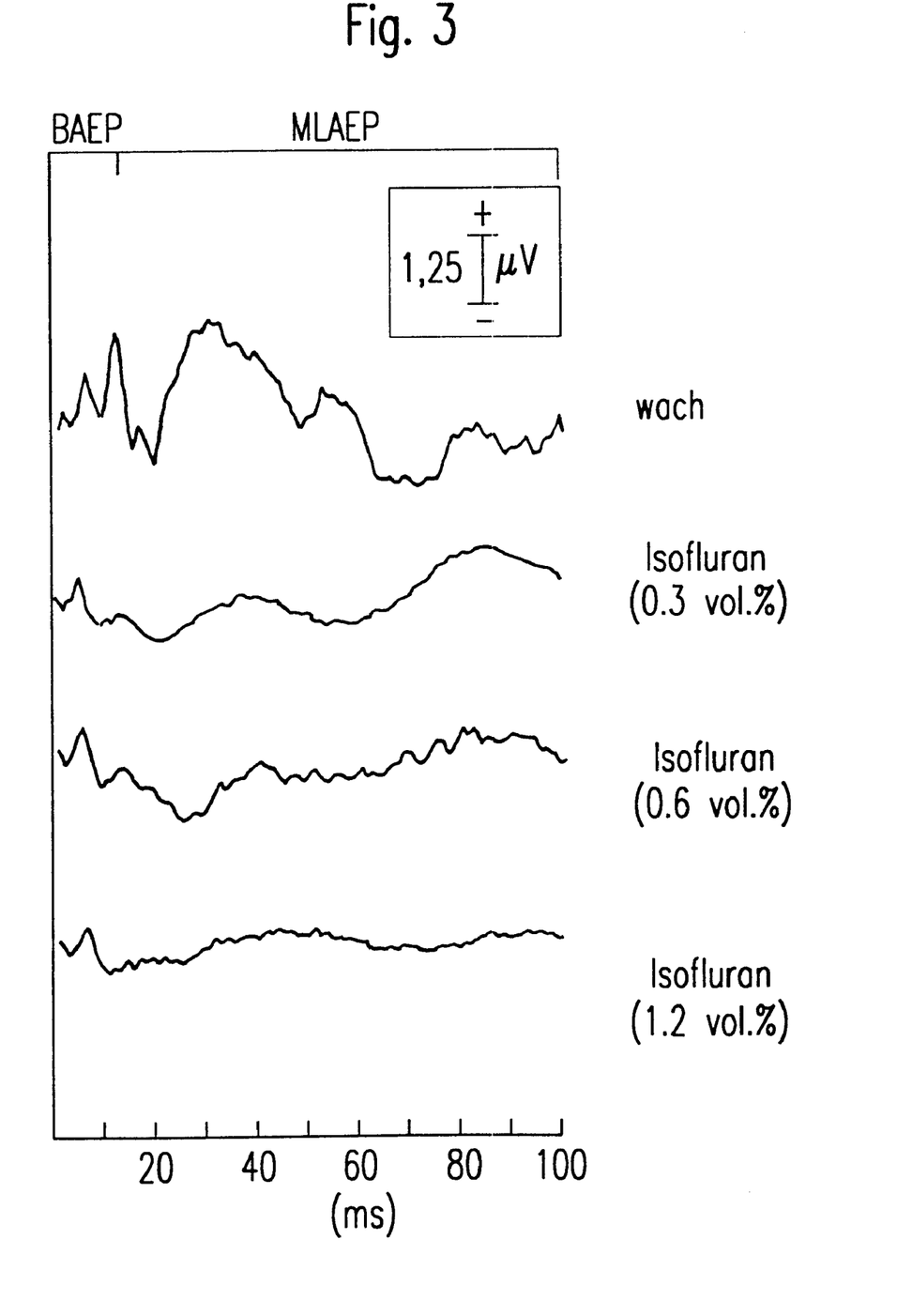
FIG. 3 illustrates dose-dependent changes of MLAEP-curves.

FIG. 3 shows a dose-dependent increase of latencies and a decrease of MLAEP amplitudes using increasing concentrations of isofluorane as an example. The curves of FIG. 3 are calculated by the computer of the evaluation unit and are displayed on, for example, a monitor. (For other cases, the invention allows to provide the curves only within the computer for automatic evaluation without having them made available visually). In practice, it is normally preferred to display not only the current BAEP and MLAEP curves recorded with narcotized patients during surgery, but also the curves recorded presurgically with patients in wake condition (FIG. 2) as well as other curves, such as the last five BAEP and MLAEP curves which subsequently occur at regular intervals, e.g. at one-minute intervals, so that in the medium run a trend can be observed (e.g. for the last five minutes prior to the current curves). The mentioned curves can be displayed simultaneously and may, for example, correspond to FIG. 3. Here, the respective current recording curve is displayed as the lowest curve, below the wake curve serving as a reference. In between, we see the previously recorded curve (e.g. over the last 10 minutes). While the bottom curve is the sliding average described in the following, the center curves indicate a medium-termed trend of varying recording signals.

The recording signals have to be averaged by the computer of the evaluation unit due to their small size and the superimposed spontaneous EEG potentials. For the BAEP curves a minimum of 1000 averages is usually required in order to assure that the information will be analyzed reliably. Even more reliable are 2000 to 4000 averages, whereas for the MLAEP a total of 500 or 1000 will be sufficient. Assuming a stimulation frequency of approximately 10 Hz and 1000 averages, a signal will be provided every two minutes. As with such long time intervals the respective changes of the signals can only be recorded with a coarse time resolution, the recording distance is decreased in compliance with the invention by determining and displaying the current curves, especially the current information curve as a sliding average. The sliding average is calculated by averaging the mean value of, for example, the last 1000 curves after every 100 sweeps. Preferably, the last 1000 artifact-free values are taken (artifacts are errors due to patient movements or external disturbances).

Figure 4:
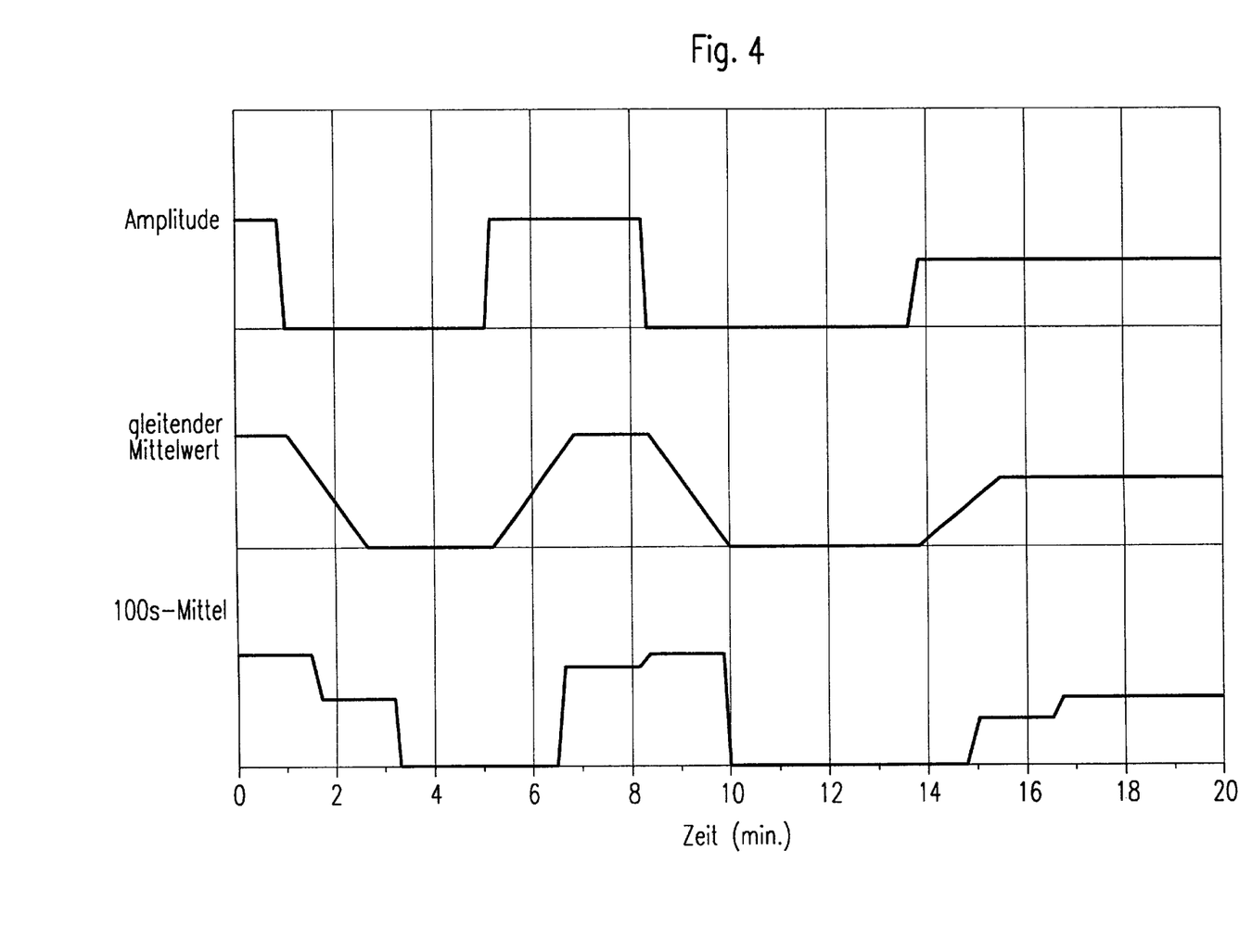
FIGS. 4, 5 and 6 are various curves used for explanation of the invention.
Figure 5:
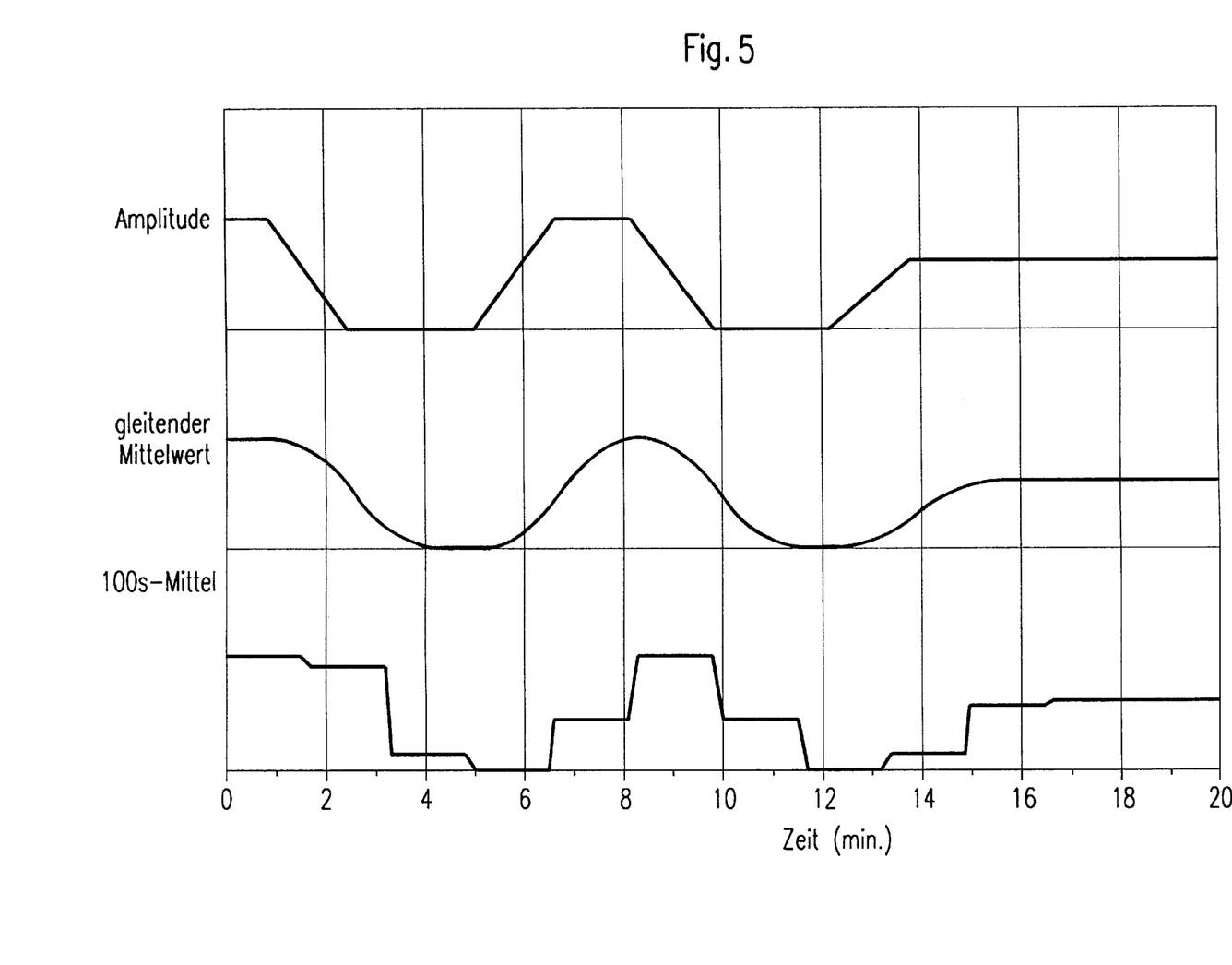

The effect on the trend display of the recorded signal amplitudes is shown in FIG. 4 with a sudden change in amplitude and in FIG. 5 with a linear change in amplitude, respectively. The upper curve of each figure represents the time trend of the actual amplitude. Below, we see the trend with a sliding average. The lowest curve shows the trend of a simple average over 100 s. As will be understood, the sliding average method is closer to the actual trend of the recording signal and will respond earlier to changes.

Figure 6:
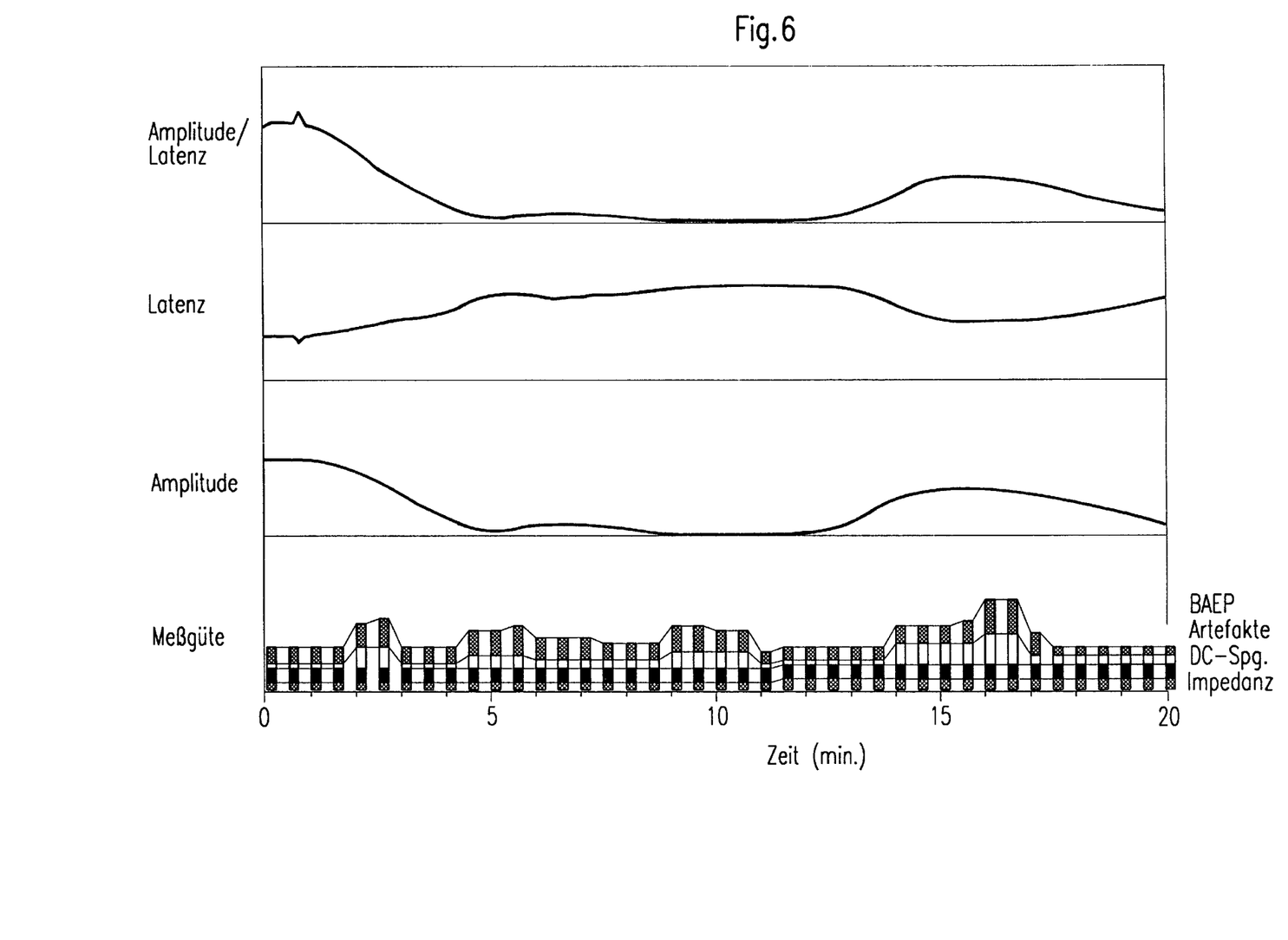
Figure 7:
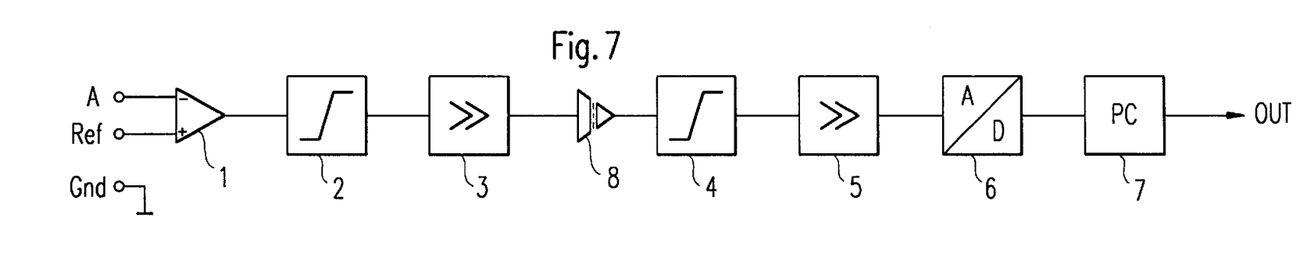
FIG. 7 is a schematic of the amplifier circuit of a test assembly complying with the invention.

A trend can also be displayed automatically as a separate diagram, as shown in FIG. 6. In this case the original curves described above, i.e. the time trend of the measured stimulus-evoked potentials, have not necessarily been made available visually; it may be sufficient to manage and analyze these curves in the computer (FIG. 7). This makes it possible to display only the trend of the automatically analyzed amplitudes and latencies and/or other information. Please see the upper curve of FIG. 6 as an example. It shows the change in time of the quotient of a specific amplitude, here peak Nb (see FIG. 1), and the related latency, whereas the actual curves of latency or amplitude are displayed therebelow. Among the relevant parameters, amplitude and latency of peak Pb are especially informative. Other characteristic information is derived from, for example, the product of latency and difference of amplitudes of specific peaks.

As shown by the graph at the bottom of FIG. 6, it is furthermore possible to display the time trend of information about the quality of the recorded signals in visual relation to the displayed recorded and/or trend values. Here, the quality of the recorded signals is calculated from electrode impedance and electrode DC voltage, frequency of artifacts, and BAEP-quality. After having measured each of these components, an assessment factor is assigned to the individual components, which are considered when calculating recording quality. Assessment factors between 1 and 10 are assigned to, for example, electrode impedances within a range of 0 and >30 k Ω, electrode direct voltage within a range of 0 and >100 m V, artifact frequency within a range of 0 and >9% and to BAEP quality.

BAEP quality can be calculated from different factors, especially from changes in correlation with the wake curve, from reliability of detecting peak V (see FIG. 1) and from deviation between smoothed and non-smoothed curves. The assessment factors may, for example, appear in the trend display individually or as a weighed product.

Furthermore, it may be useful to display automatically calculated time and/or amplitude markings and/or other numbers in connection with the shown curves.

Success of the described method will depend largely on the reliability of the recordings. In case of monitoring of anesthesia the anesthetist will in most cases not be able to interpret the curves. If the recorded signals are distorted, for example, due to artifacts, the anesthetist may draw wrong conclusions. The system described so far will automatically check the reliability of recordings by measuring the electrode impedance in regular intervals, checking the DC voltage at the electrodes by artifact detection and suppression as well as reference comparison.

An electrode impedance check is a common feature during long-term recording of biological signals. The measurement is performed at a fixed frequency of, for example 100 Hz, or with direct current. When exceeding a limit value, a warning signal will be generated.

Regular measurement of electrode direct current is known, too. With the system described this feature is required because considerably high direct voltages (up to 500 mV) may be produced at the electrode side if bad electrodes or different electrode material is used. This may generate voltages when cables and/or electrodes are displaced due to changes in capacities between cables and changes of the electrode/skin contact. These voltages will be superimposed on the signal to be measured. As a result, movement artifacts will occur, which may disturb signal recording. If the direct voltages become too high, they can saturate DC-coupled amplifiers so that the signal will be distorted, or decreased or may disappear completely.

As mentioned above, signals with artifacts are to be neglected during averaging. Often measurements are distorted due to signals which are within the transfer range of the recording signal but do not correspond to its shape in a way that analysis errors will occur. For example, the actual course of the recorded potentials can be distorted by a superimposed 50 Hz or 60 Hz mains interference signal.

Resulting recording errors can be avoided by means of frequency analysis, which is especially effective with constant frequency interference and/or by means of cross correlation with a known "good" curve. For the system described, the constant BAEP signal which is independent of dose, is especially suited. In case of dose-dependent signals, such as the MLAEP, frequency analysis as well as cross-correlation between partial sum signals are to be preferred. Consequently, the automatic comparison of frequency contents and/or cross correlation to reference and/or partial sum signals is a further important criterion for assessing recording quality.

Besides, the BAEP curve may be used as a reference for assessing the recording conditions. Interference signals can be immediately detected in the BAEP curve. Comparison of the currently recorded BAEP curve with a known "good" curve, such as the curve measured before surgery, allows for an assessment of the recording conditions and consequently of recording quality. This comparison may be performed either visually or automatically by the processing system.

Furthermore, good and reliable recording of the signals to be displayed in particular depends on the amplification method used. During recording of evoked potentials, i.e. of voltages between 0.5 and 10 $\mu V$, which are additionally superimposed by spontaneous EEG potentials, the amplifiers have to be as linear as possible, low noise and free of intermodulation. In addition, a high common mode rejection is required. The transmission lines from the site of recording to the amplifier have to be as short as possible and must be protected against interference potentials. An amplifier circuit, meeting these requirements, can be see in FIG. 7. It contains an instrumentation amplifier stage 1 which serves as an input stage, amplifies the incoming signal and transfers it via a high-pass filter 2, a mid-amplifier 3, a low-pass filter 4 and a post-amplifier 5 via an A/D (analog to digital) converter 6 to an evaluation unit 7 normally represented by a PC or other computer. So far, the amplifier of the described system is equal to known circuits. With the invention, the isolation stage 8, which is employed for galvanic and physical isolation between the amplifier unit at the patient side and the amplifier unit at the side of the evaluation system, is connected to the output of the amplifier stage 3 after high pass filter 2. This provides the advantages already mentioned above. Gain of the pre-amplifier unit stage 3 is set in a way that the full-scale output signal will always amount to at least some milivolts at a full-scale input range of, for example, 10 $\mu V$. On the one hand, this value assures that signal distortion due to crossover distortions of amplifier stage 3 will remain below the relevant limits. On the other hand it is guaranteed that the signal to noise ratio is sufficient and that the output signals will not considerably interfere with the input signals. In other words: Total gain of the amplifier unit connected between the electrode assembly and isolation stage 8 is to be considerably higher than 100, but less than $10^4$ and should preferably amount to approximately 1000 to 2000 and maximally to 4000.

Isolation stage 8 is an active circuit. It can, for example, be an isolation amplifier functioning on the basis of capacitive coupling and signal modulation, which can be bought as an integrated circuit (type ISO, manufactured by Burr Brown). Instead, an optoelectronic decoupling amplifier or a circuit functioning on the basis of signal modulation and demodulation before and after magnetic decoupling (e.g. isolation amplifier AD 215, manufactured by Analog Device) can be used.

In our example, the electrode assembly consists of the two recording electrodes A and Ref, each connected to the two inputs of input stage 1 and to a ground electrode Gnd. The recording electrode A is referred to as the active electrode, which is attached to a position where the brain potentials can be recorded best. The electrode Ref serves as a reference electrode and is attached to the patient at a position where the potentials will have no effect. The ground electrode Gnd can be attached at any position desired.

High pass 2 and low-pass 4 are set in a way such that the frequency spectrum of the BAEP and MLAEP curve will provide any desired information. It is possible to record and transfer both signals in the same frequency band, e.g. between 10 Hz and 3 kHz. Consequently, transfer will be optimal for both signals. In this case, the high-pass 2 will be set to 10 Hz and the low-pass 4 to 3 kHz. If both signals are transferred via the same channel, only a minimum amplifier expenditure is required. Evaluation unit 7 filters the recorded signals so that the BAEP and MLAEP signals will be presented with prime quality. For the BAEP signals this is a frequency range typically of 100 to 3000 Hz, for MLAEPs a range of 10 to 200 Hz. Good recording results will be achieved with digital filtering or other methods of digital processing.

A further method for preprocessing recording signals is to record and process BAEP and MLAEP potentials via two separate channels.

Reliable recording, amplification and display of the recorded can best be assured if impedances of the electrodes connected to the patient are correct. The impedance circuit intended to be used with the test assembly described so far will provide a further improvement as compared with commonly used circuits.

Figure 8:
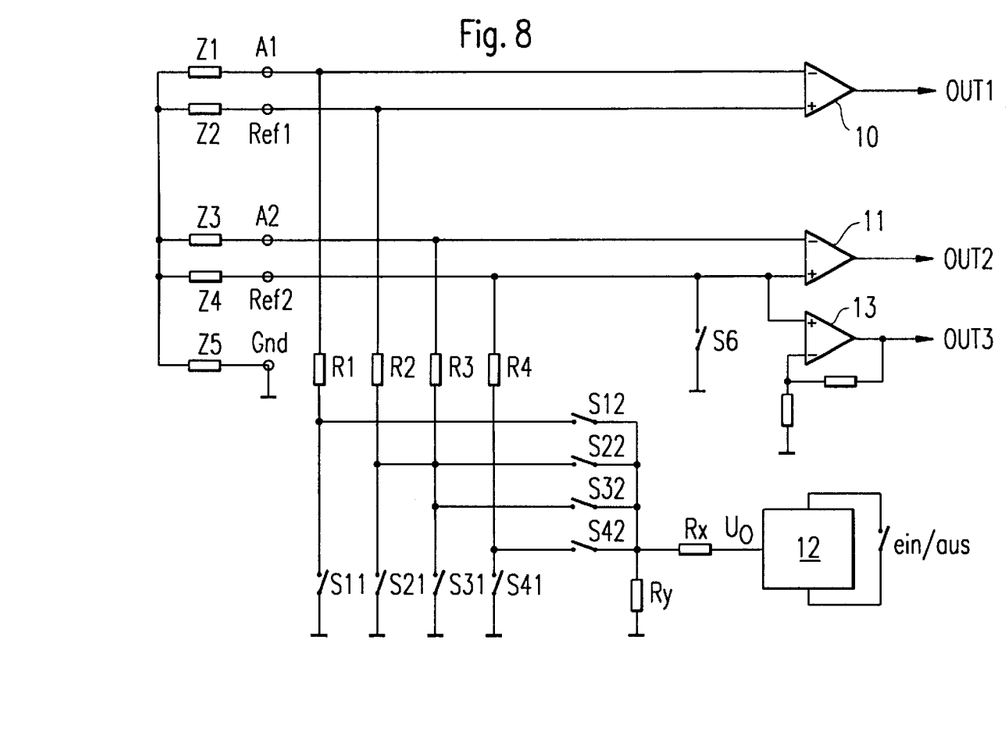
FIG. 8 is a schematic circuit configuration for recording of electrode impedance of the test assembly.

For impedance measurement the invention uses the input terminating resistors of the amplifier for applying a test current. FIG. 8 shows a preferably used model consisting of a two-channel assembly, making it possible to measure impedance of all electrodes of two separate amplifier circuits 10 and 11. The impedances of electrode A1 and Ref1 of the amplifier 10 are referred to as Z1 and Z2, whereas Z3 and Z4 stand for the electrode impedance of the pickup electrodes A2 and Ref2 of the amplifier 11. Z5 is the impedance of the common ground electrode Gnd. The inputs of each of the two amplifiers 10 and 11 can be grounded via the input terminating resistances R1, R2, R3 or R4 respectively. Between ground and each of the input terminating impedances there is a first switch S11, S21, S31 or S41. A second switch S12, S22, S32 or S42 can be connected between the connection of the input terminating resistances with the first switches and a test current generator 12 (see FIG. 8).

Voltage of generator 12 can either be taken off directly or via a voltage divider represented by resistors Rx and Ry in FIG. 8. Voltage divider Rx/Ry is to be preferred, as probably existing interferences from the decoupled generator 12 can be better kept off the amplifier input lines.

With a recording frequency (of the recorded signal) of typically 100 Hz the electrode impedances will normally be below 100 k $\Omega$ (higher impedances are not suitable for recording evoked potentials), while the input terminating resistors are normally within a range of 10 and 100 M k $\Omega$.

For measuring, for example, impedance of the active electrode A1 of the first channel, switch S11 is opened, S12 is closed and the test current generator 12 is switched on. The test current I1 now passes to the input of the active electrode A1 via the resistance R1.

$$I1=U_0/(R1+Z1)\approx U_0/R1$$

The test current generates a voltage drop of I1 Z1 across Z1, which is amplified by amplifier 10. The subsequent electronic assembly makes it possible to determine electrode impedance. The measurement of electrode impedances Z2, Z3 and Z4 is performed similarly.

For recording impedance Z5 of the ground electrode Gnd, three possibilities can be used. Those possibilities are a short circuit of an input to ground, taking off the voltage at Z5 via a separate amplifier, or taking off the voltage by part of one of the amplifiers 10 or 11.

According to the first possibility, one of the inputs A1, Ref1, or A2 or Ref2 is grounded via a further switch S6. The example in FIG. 8 shows switch S6 connected to the input of amplifier 11, which is connected to the reference electrode Ref2. Here, the test current can be fed into electrode A1 or Ref1 or both electrodes simultaneously. Amplifier 11 is now able to measure the voltage drop across electrode impedance Z5. It can also be considered to allow the test current to pass to the active electrode A2, which will result in a voltage drop at the input of amplifier 11 proportional to the sum of the impedances Z3 and Z5.

According to the second possibility, the voltage across Z5 can be picked up and amplified by an additional operational amplifier 13 connected in parallel to one of the amplifier 10 or 11. The example in FIG. 8 shows one of the inputs of amplifier 13 connected to the input of amplifier 11 which is connected to reference electrode Ref2. The test current can be fed into one or several inputs which are connected to electrodes A1, Ref1 or A2. For picking up the voltages at one of the other inputs the test current will be fed into one or more of the remaining inputs (see example).

According to the third possibility, the voltage across Z5 can be picked up at one of the amplifiers 10 or 11 themselves, if its input stage is suited for this task. An example can be seen in FIG. 9.

Figure 9:
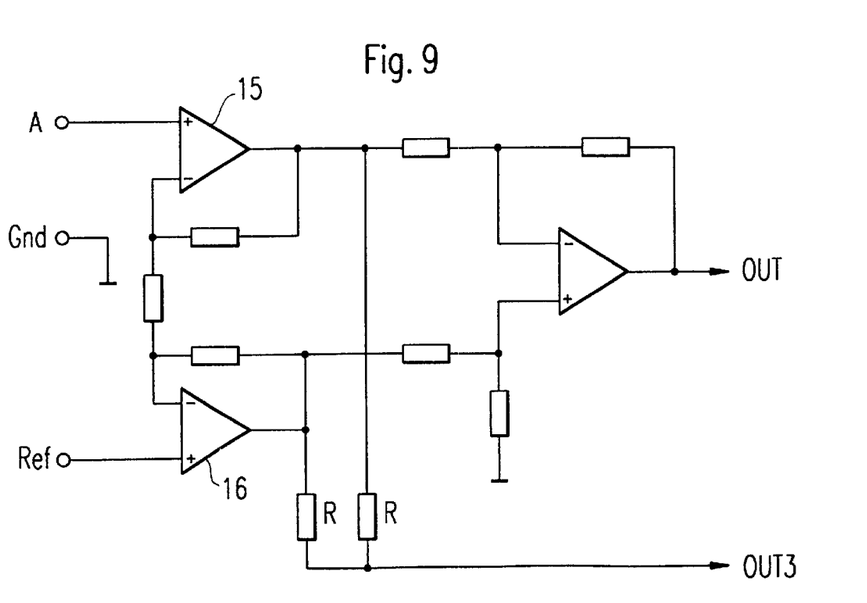
FIG. 9 is a typical layout of the amplifier circuit input stage according to FIG. 2.

The input stage consists of two operational amplifiers 15 and 16 one input of each is connected to one of the two electrodes A and Ref and the remaining inputs are interconnected. The outputs of the two amplifiers 15 and 16 are connected with a common output OUT3 for the impedance test signal via one resistance R each. Voltage at Z5 corresponds to a common mode voltage at the inputs and/or the electrodes A and Ref of the amplifier unit. This common mode voltage is led to output OUT3 via the resistances R. Voltage can also be taken off directly at the output of one of the two operation amplifiers 15 or 16, if the differential signal between A and Ref is considerably smaller than the common mode signal caused by the voltage drop across Z5.

For recording the test signals the switches S11, S21, S31 and S41 are closed whereas switches S21, S22, S32 and S42 (FIG. 8) are opened.

The described test assembly can be expanded to any desired number of channels or reduced to a single channel. With assemblies of two or more channels it can be useful to connect several Ref inputs of the amplifiers to one common electrode, which will considerably reduce the expenditure required for electrode impedance recording. For the interconnected Ref inputs a buffer my be introduced.

The described assembly has the advantage that the input impedance of the instrumentation amplifiers serving as an amplifier circuit for evoked potentials is clearly defined during recording and that interferences are not induced to the input circuit via the generator and the input resistances.

As a conclusion, by the method described a miniaturized pre-amplifier is created which is sufficiently insensitive against interference from the test environment.

What is claimed is:

1. A method for measurement and coherent display of stimulus-evoked potentials of the brain of a patient comprising the following steps:

A. providing at least two pickup electrodes;

B. mounting at least one of the pickup electrodes on an appropriate site on the patient to develop a variable information signal corresponding to evoked potentials of the patient, which potentials are responsive to stimuli applied to the patient and are representative of a given neurophysiological function of the patient;

C. mounting at least one of the pickup electrodes on an appropriate site on a patient to develop a base information signal representative of brainstem-evoked potentials of the patient, which potentials are essentially independent of the given neurophysiological function of the patient;

D. simultaneously displaying the variable and base information signals for comparison with each other, the display of the base information signal having a higher time resolution than the display of the variable information signal;

E. repeating the stimuli evoking the potentials of the patient during given periods of time;

F. averaging the variable and base information signals over a time duration considerably greater than each of said given periods;

G. and displaying after each of said given periods the signals averaged over said greater time duration in the manner set forth in step D.

2. A method for measurement and coherent display of stimulus-evoked potentials of the brain, according to claim 1, comprising the following sub-steps F1–F3 during Step F:

F1. averaging the variable and base information signals over predetermined periods of time;

F2. comparing a number of the averaged signals of sub-step F1 with each other; and F3. averaging the signals averaged in sub-step F1, any averaged signals differing substantially in Step F2 from the majority of the other averaged signals being neglected.

3. A method for measurement and coherent display of stimulus-evoked potentials of the brain, according to claim 1, in which the neurophysiological function of the patient is anaesthesia of the patient.

4. A method for measurement and coherent display of stimulus-evoked potentials of the brain, according to claim 3, comprising displaying simultaneously, during Step D, the information signals developed with the patient at wake, the information signals developed thereafter at regular intervals, and the information signals currently developed at the time of display.

5. A method for measurement and coherent display of stimulus-evoked potentials of the brain of a patient undergoing anaesthesia comprising the following steps:

M. providing at least two pickup electrodes;

N. mounting at least one of the pickup electrodes on an appropriate site on the skull of a patient to develop a series of base information potentials representative of brainstem auditory-evoked potentials (BAEP) of the patient, which potentials are essentially independent of anaesthesia applied to the patient;

O. amplifying and filtering the base information potentials to develop a base information signal;

P. mounting at least one of the pickup electrodes on an appropriate site on the skull of the patient to develop a series of variable potentials representative of mid-latency auditory-evoked potentials (MLAEP) of the patient, which potentials are responsive to anaesthetic stimuli applied to the patient;

Q. amplifying and filtering the variable information potentials to develop a variable information signal;

R. simultaneously displaying the base and variable information signals for comparison with each other, the display of the variable information signal having a lower time resolution than the display of the base information signal; and, during Step R, displaying the time trend of changes of at least one of given characteristic values of the variable information signal, said characteristic values including a characteristic peak (Nb) of the variable information signal, its latency, and the quotient of these two factors.

6. A system for measurement and display of stimulus-evoked potentials of the brain of a patient comprising:

at least one pickup electrode, mountable on a patient, for developing potentials representative of brain potentials of the patient;

a coupling circuit, having an input connected to the pickup electrode, for developing a variable information signal corresponding to evoked brain potentials representative of a given neurophysiological function of the patient, the coupling circuit including, in series, a first filter and amplifier stage, an isolation stage, and a second filter and amplifier stage;

and a computer display circuit for displaying the information signal in a variable time-base display;

the computer display circuit displaying brainstem-evoked potentials simultaneously with the evoked brain potentials representative of the function but with the time base of the brainstem-evoked potentials expanded with respect to the brain potentials representative of the function; and the brainstem-evoked potentials being displayed with a higher amplitude resolution as compared with the potentials representative of the neurophysiological function of the patient.

7. A system for measurement and display of stimulus-evoked potentials of the brain of a patient, according to claim 6, in which at least two information signals representative of mid-latency auditory-evoked potentials (MLAEP) are displayed simultaneously to indicate a time trend therefor.

8. A system for measurement and display of stimulus-evoked potentials of the brain of a patient, according to claim 6, in which the coupling stage, from the pickup electrode to the computer stage, includes in series:

an input amplifier;

a high-pass filter;

an isolation amplifier;

a low-pass filter; and an output amplifier.

9. A system for measurement and display of stimulus-evoked potentials of the brain of a patient comprising:

at least one pickup electrode, mountable on a patient, for developing potentials representative of brain potentials of the patient;

a coupling circuit, having an input connected to the pickup electrode, for developing a variable information signal corresponding to evoked brain potentials representative of a given neurophysiological function of the patient, the coupling circuit including, in series, a first filter and amplifier stage, an isolation stage, and a second filter and amplifier stage;

and a computer display circuit for displaying the information signal in a variable time-base display;

said display circuit being galvanically isolated from the pickup electrode by said isolation stage;

the total gain of the coupling circuit being at least approximately $10^5$;

and the total gain of the first amplifier stage being in the range of approximately $10^3$ to $4 \times 10^3$.

10. A system for measurement and display of stimulus-evoked potentials of the brain of a patient, according to claim 9, in which the first filter and amplifier stage includes a high-pass filter and the second filter and amplifier stage includes a low-pass filter.

11. A system for measurement and display of stimulus-evoked potentials of the brain of a patient, according to claim 10, in which the cut-off frequency of the high-pass filter is about 10 Hz and the cut-off frequency of the low-pass filter is about 3 kHz.

12. A system for measurement and display of stimulus-evoked potentials of the brain of a patient, according to claim 9, and further comprising an impedance measuring circuit connectable to the pickup electrode for measuring the impedance of the electrode, the measuring circuit including a test current generator.

13. A system for measurement and display of stimulus-evoked potentials of the brain of a patient, according to claim 12, wherein an input terminating resistor is coupled between the pickup electrode and a reference potential point, and the measuring circuit further includes a first switch coupled between the input terminating resistor and said reference potential point, and a second switch coupled between the input terminating resistor and the test current generator.

* * * * *